United States Patent
Osypka

(10) Patent No.: US 9,265,937 B2
(45) Date of Patent: Feb. 23, 2016

(54) IMPLANTABLE INDIFFERENT REFERENCE ELECTRODE POLE

(71) Applicant: Peter Osypka, Grenzach-Wyhlen (DE)

(72) Inventor: Peter Osypka, Grenzach-Wyhlen (DE)

( * ) Notice: Subject to any disclaimer, the term of this patent is extended or adjusted under 35 U.S.C. 154(b) by 137 days.

(21) Appl. No.: 13/912,585

(22) Filed: Jun. 7, 2013

(65) Prior Publication Data
US 2013/0331920 A1    Dec. 12, 2013

(30) Foreign Application Priority Data

Jun. 11, 2012 (EP) .................................... 12004397

(51) Int. Cl.
*A61N 1/05* (2006.01)

(52) U.S. Cl.
CPC .............. *A61N 1/0587* (2013.01); *A61N 1/057* (2013.01); *A61N 1/059* (2013.01); *A61N 1/0568* (2013.01)

(58) Field of Classification Search
CPC ..... A61N 1/059; A61N 1/057; A61N 1/0587; A61N 1/0568
USPC ......................... 607/120, 127, 122
See application file for complete search history.

(56) References Cited

U.S. PATENT DOCUMENTS

| | | | |
|---|---|---|---|
| 5,855,592 A | 1/1999 | McGee et al. | |
| 7,450,999 B1 | 11/2008 | Karicherla et al. | |
| 7,515,971 B1 | 4/2009 | Doan | |
| 2008/0082132 A1* | 4/2008 | Annest et al. | 607/4 |

FOREIGN PATENT DOCUMENTS

| | | |
|---|---|---|
| DE | 202010011492 U1 | 10/2010 |
| DE | 202011108639 U1 | 1/2012 |

* cited by examiner

*Primary Examiner* — Alyssa M Alter
(74) *Attorney, Agent, or Firm* — Locke Lord LLP; Scott D. Wofsy; Arpita G. Buesing

(57) ABSTRACT

An implantable electrode device designed for heart stimulation and/or cardioversion/defibrillation in connection with a pacemaker or a defibrillator. The electrode device comprises a large-surface area indifferent reference electrode pole permanently implanted in the atrial septum and in electrical communication with a pacemaker or defibrillator. The electrode pole is made from biocompatible metal braiding and has a tube like opening. The electrical communication is positioned from the pacemaker/defibrillator via the right atrium of the heart through the indifferent electrode pole into the left atrium via the opening. Thus allowing electrical pulses to be delivered to the electrode pole and stimulating the heart.

12 Claims, 9 Drawing Sheets

IMPLANTABLE INDIFFERENT REFERENCE ELECTRODE POLE

CROSS-REFERENCE TO RELATED APPLICATIONS

This application claims under 35 U.S.C. §119(a) priority to and benefit of European Patent Application No. EP12004397 filed Jun. 11, 2012, which is incorporated by reference herein in its entirety.

BACKGROUND OF THE INVENTION

1. Field of the Invention

The present invention relates to an implantable indifferent reference electrode pole and more particularly an electrode pole which can be used to facilitate both stimulation and cardioversion/defibrillation of all four heart chambers.

2. Description of Related Art

Implantable pacing leads are known since about 1960, the time when the first pacemaker was implanted. The use of pacemakers has continued to grow during the 1970s due to improved reliability and, in particular, higher breakage resistance of the electrode devices and due to good fixing of the electrode-tip in the right atrium. However, pacing therapy for treating congestive heart failure often requires left ventricular or left atrial stimulation, either alone or in conjunction with right ventricular stimulation and defibrillation usage.

Left ventricular access leads have been developed which are introduced through the coronary sinus and then advanced through the coronary veins so that an electrode can be positioned on the surface of the left ventricle near the apex of the heart.

For permanent stimulation of the left heart chambers, especially the left atrium there is as yet no simple solution. It would therefore be beneficial to provide a quick and easy access via the intra-atrial septum to the left atrium and the left ventricle further providing the possibility of exact positioning of the electrode during stimulation or cardioversion/defibrillation, thus giving the chance for a successful therapy of atrial and ventricular fibrillation.

Such conventional methods and systems have generally been considered satisfactory for their intended purpose. However, there is still a need in the art for an implantable indifferent electrode pole that allows for facilitation of stimulation for all four heart chambers. The present invention provides a solution for these problems.

SUMMARY OF THE INVENTION

The subject invention is directed to a new and useful implantable indifferent reference electrode device.

In one aspect of the present invention an implantable electrode device is disclosed. The electrode device is designed for heart stimulation and/or cardioversion/defibrillation in connection with a pacemaker or a defibrillator. The electrode device comprises a large-surface area indifferent reference electrode pole permanently implanted in the atrial septum and in electrical communication with a pacemaker or defibrillator. The electrode pole is made from biocompatible metal braiding and has a tube like opening. The electrical communication is positioned from the pacemaker/defibrillator via the right atrium of the heart through the indifferent electrode pole into the left atrium via the opening. Thus allowing electrical pulses to be delivered to the electrode pole and stimulating the heart. Preferably, the electrode pole is shaped like an occlusion element being self-expandable and forming a double disc which bridges the left and right atrium.

A stent may be placed in the tube like opening. Alternatively, the tube like opening may comprise a seal member disposed within. The seal member may contain a drug formulation.

The opening of electrode pole has a proximal end and a distal end, the proximal end near the right atrium is attached to an elongated tube. At least one coil may be disposed within an inner part of the elongated tube.

In another aspect of the present invention the electrical communication to the electrode pole is placed at the outer edge of the braiding.

In yet another aspect of the present invention, the braiding of electrode pole is fitted with a fixation element in form of a screw coil. Alternatively, the braiding of electrode pole is fitted with a fixation element in form of a spread hook fastening element.

In another aspect of the invention, at least one part of the braiding of electrode pole is coated with a biocompatible polymer layer.

In yet another aspect of the invention a pacing electrode tip pole is inserted via the opening into the left atrium. The tip pole has a distal screw electrode such that the left atrium is stimulated between the electrode device and the screw electrode.

In another aspect of the present invention, a method for treatment of patients with atrial fibrillation is disclosed. The method comprises implanting an electrode device into the atrial septum, the electrode device including an indifferent reference electrode pole having a tube like opening. Next, the electrode pole is connected to a pacemaker/defibrillator via the right atrium of the heart. A screw tip pole is advanced through the tube like opening and implanted into the left atrium of the heart. Finally, the pacemaker/defibrillator is activated to stimulate the left atrium of the heart between the electrode pole and the screw tip pole.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1:
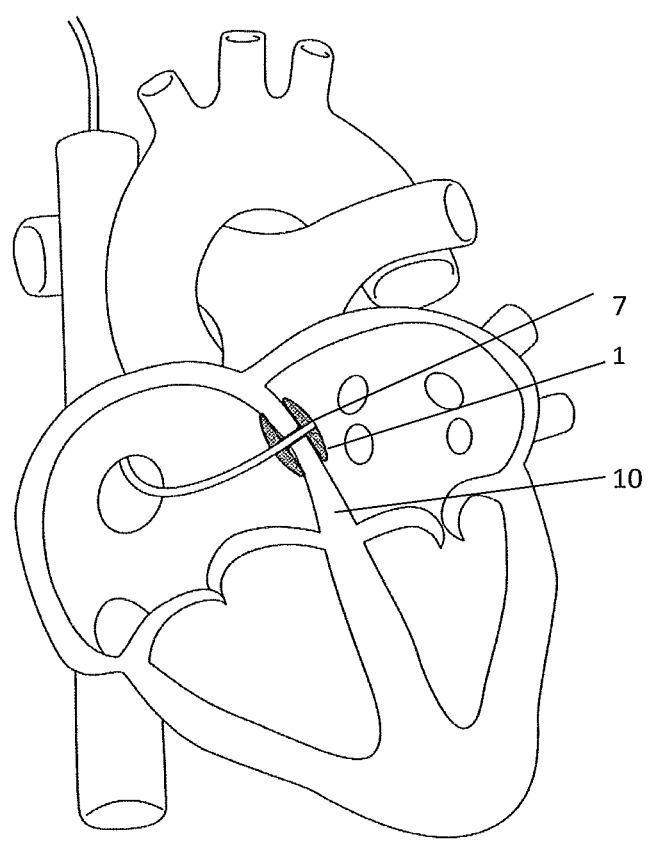
FIG. 1 is a perspective view of the implantable indifferent reference electrode pole according to the invention implanted in the atrial septum forming a double disc with a tube like opening.

Reference will now be made to the drawings wherein like reference numerals identify similar structural features or aspects of the subject invention. For purposes of explanation and illustration, and not limitation, a partial view of an exemplary embodiment of the implantable indifferent reference electrode device in accordance with the invention is shown in FIG. 1. The system of the invention can be used for providing stimulation to all four heart chambers.

FIG. 1 shows an exemplary electrode device having an indifferent reference electrode pole 1 implanted in the atrial septum 10. The electrode pole 1 is braided from threads made from biocompatible metal, preferably memory metal threads like Nitinol wires. The braiding may consist of one single wire braiding or a double or multi wire braiding. The braiding may have different sizes and shapes. Preferably, the braiding is circular or elliptical. The electrode pole 1 is shaped comparable to an occlusion element for unwanted openings in the heart for atrial-septal defects (ASD) and its placement is similar to the placement of an ASD occluder as described in U.S. Patent Application No. 2009/0281567 or an PFO (patent foramen ovale)-occluder as described in U.S. Patent Application No. 2007/0150000, both of which are incorporated by reference herein.

The electrode pole 1 is preferably of umbrella shape forming a double disc which bridges the left and the right atrium. Electrode pole 1 includes a tube like opening 7. The electrical connection to the pole is placed via the right atrium of the heart and further up in the venous blood vessel system such as in the vena subclavia allowing pacing pulses to be delivered to the pole when a pacemaker is connected. Thus, electrode pole 1 functions as an indifferent electrode for both the left and right atria.

Electrode pole 1 is implantable in a simple manner using, for example, a suitable insertion catheter. The insertion catheter system is advanced to the septum of the right atrium. By means of a puncture of the septum of the atrium, which can be, for example, a known transseptal puncture, the left atrium of the heart is reached.

Figure 2:
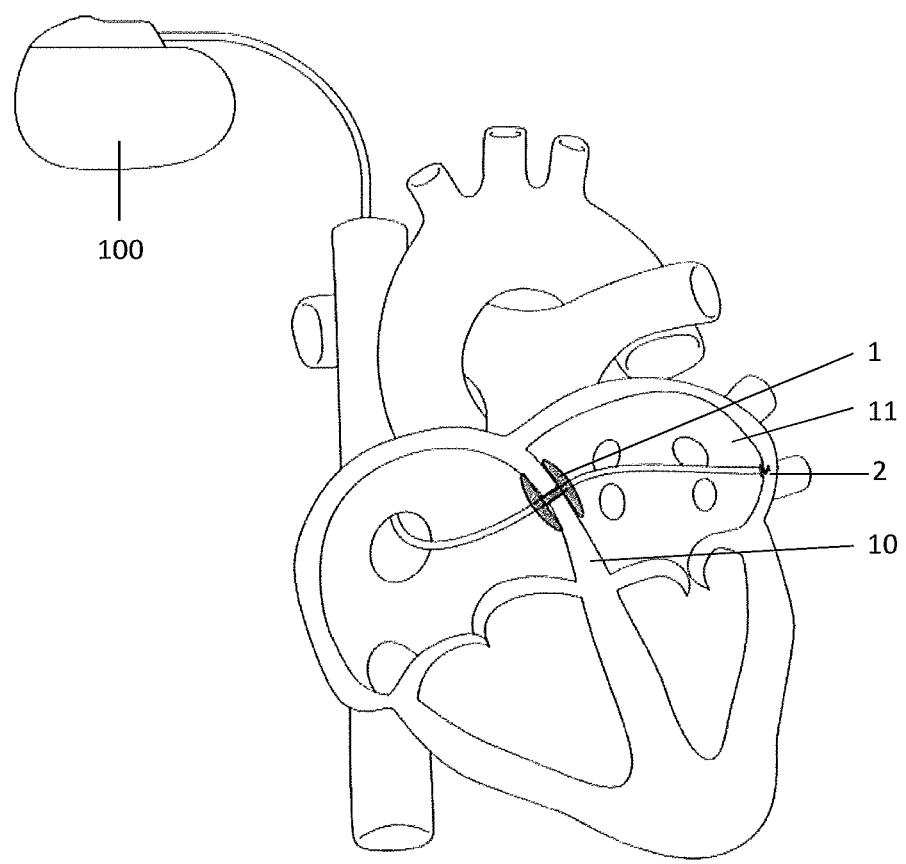
FIG. 2 is a perspective view of the electrode pole of FIG. 1, showing a pacing electrode inserted via the tube like opening into the left atrium and functioning as different electrode pole.

FIG. 2 shows the electrode pole 1 of FIG. 1, and in addition to FIG. 1, a pacing electrode tip-pole being inserted via the opening 7 into the left atrium and functioning as different electrode pole. The pacing electrode has a distal screw tip pole 2 implanted in the left atrium 11 of the heart. The electrode pole 1 is an indifferent electrode and has a central opening serving as a passage opening for the screw electrode tip pole 2. The stimulation of the left atrium is between electrode pole 1 and the tip pole 2 of the screw electrode. Screw electrodes are known in the art and are used as pacing electrodes since about 35 years. Screw tip electrodes are especially suitable to be placed in the atria of the heart because they can be easily affixed in any place of the heart and do not move after being carefully placed. As shown, the electrode device is connected to a pacemaker/defibrillation 100.

Figure 3A:
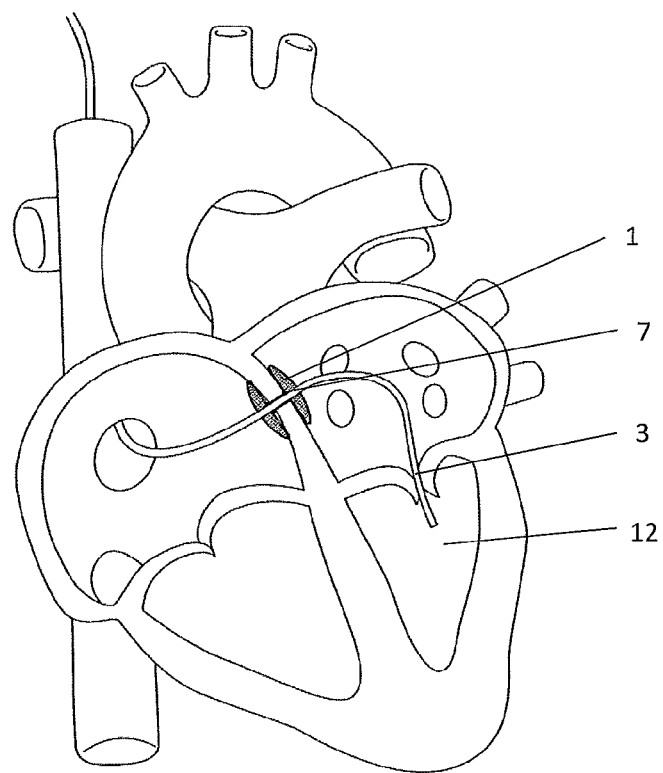
FIGS. 3a and 3b are perspective views of the electrode pole of FIGS. 1 and 2, illustrating how access to the left ventricle is provided.

FIG. 3a shows the electrode pole 1 of FIGS. 1 and 2 and in addition shows how access to the left ventricle 12 is provided. Electrode catheter 3 is placed into the left ventricle 12 of the heart. In general terms, opening 7 provides access for catheters or devices intended to be placed in any part of the left side of the heart.

Figure 3B:
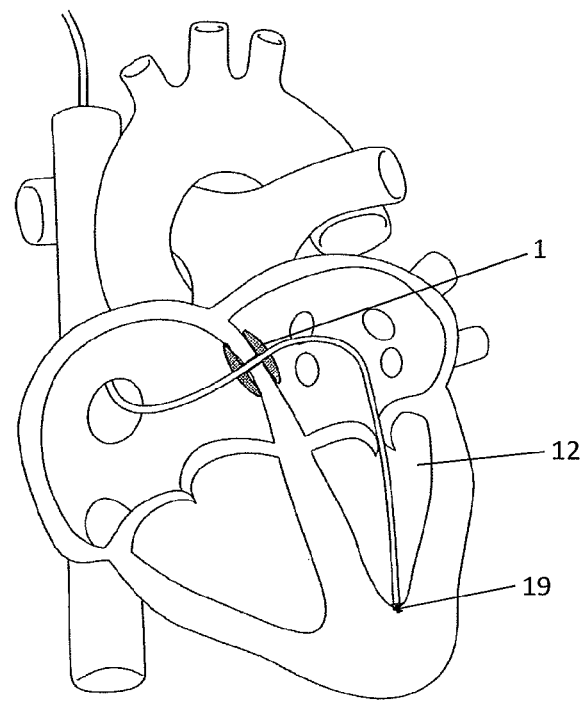

FIG. 3b shows a screw tip-pole 19 being inserted into the left ventricle. Thus, stimulation of the left ventricle 12 is possible due to pulses between electrode pole 1 and screw tip-pole 19.

Figure 4:
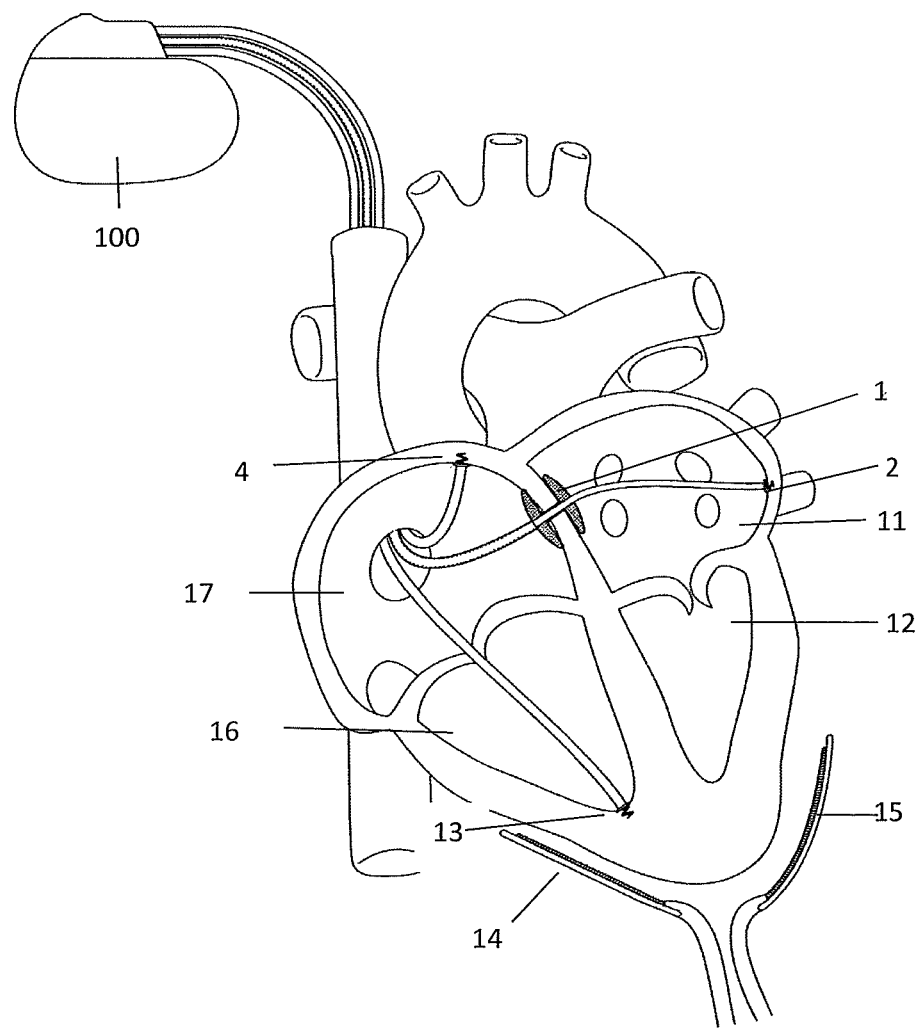
FIG. 4 is a perspective view the electrode pole of FIGS. 1 and 2 and in addition shows a number of combinations of pace/sense electrodes.

FIG. 4 shows the electrode pole 1 of FIGS. 1, 2 and 3 and in addition shows how the pace/sense electrodes, preferably screw electrodes and the indifferent electrode pole 1 can be selectively employed to provide a number of pace/sense electrode combinations for atrial/biatrial, ventricular/biventricular pacing and sensing or for pacing and sensing all four heart chambers as shown:

Stimulation of the right atrium 17: Pulses between different electrode tip-pole 4 and indifferent electrode pole 1.

Stimulation of the right ventricle 16: Pulses between different electrode tip-pole 13 and indifferent electrode pole 1.

Stimulation of the left atrium 11: Pulses between different electrode tip-pole 2 and indifferent electrode pole 1.

Stimulation of the left ventricle 12: Pulses between electrode tip pole 19 shown in FIG. 3b and electrode pole 1.

Defibrillation of the whole heart: Pulses between electrodes 14, 15 and electrode pole 1.

Cardioversion in case of atrial fibrillation: Pulses between electrode poles 4, 2 and electrode pole 1.

Figure 5:
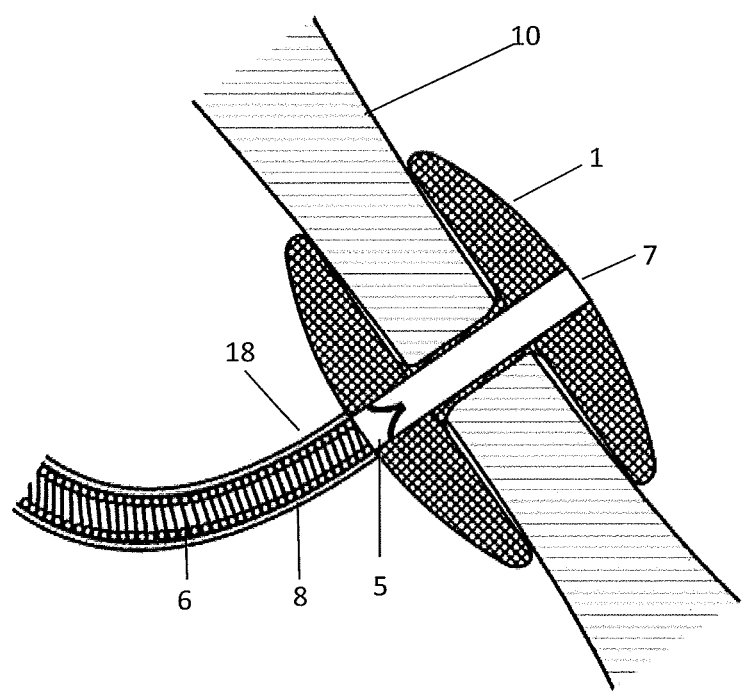
FIG. 5 is a detailed view of the electrode pole of FIG. 1.

FIG. 5 shows the electrode pole 1 of FIG. 1 implanted in the atrial septum 10 in detail. The centrally arranged tube like opening 7 has a proximal and a distal end. The proximal end is near the right atrium and is attached to an elongated tube 18. The electrical connection from the electrode pole 1 to pacemaker/defibrillator is a coil 6 insulated by silicone or polyurethane. The coil 6 may also function as a guide catheter creating access to the left heart chambers. The proximal part of the coil 6 leads with its own feed line via a venous blood vessel such as e.g. vena subclavia to a plug (e.g. a commonly known IS-1 connector) of the cardiac pacemaker/defibrillator. Furthermore, the proximal part of the coil 6 may be coupled to a port system allowing access to the left atrium if required. In alternate embodiments, the inner part of the elongated tube 18 may comprise braiding of wires and/or filaments made of metal.

The electrode pole 1 is braided and is shaped comparable to an occlusion element arranged in the septum between the two cardiac atria allowing tissue ingrowth typically within a few weeks. The tube like opening 7 may comprise a valve 5 in order to stop the shunting of blood between the atria. Opening 7 creates access to the left atrium and the left ventricle and allows the insertion of a catheter or an electrode for stimulation or defibrillation of the left heart chambers. The valve 5 preferably made of silicone may contain a drug formulation, e.g. Paclitaxel, to prevent the closing of the opening due to tissue ingrowth. With continued reference to FIG. 5, opening 7 is affixed centrally, however, if required opening 7 may be affixed elsewhere. Opening 7 provides a simple, quick and easy access to the left atrium and the left ventricle, said easy access being particularly advantageous for operations on the mitral valve and for RF-ablation of the left atrium and pulmonary vein ablation.

Figure 6:
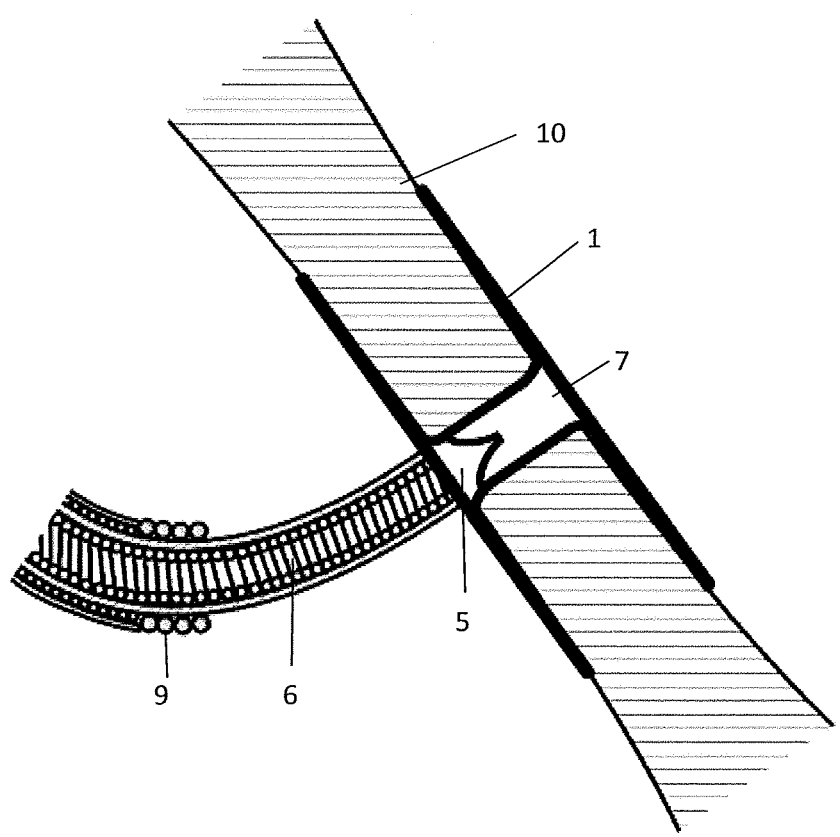
FIG. 6 is an alternate embodiment of a detailed view of the electrode pole of FIG. 1, showing a second electrode in form of a metallic coil surrounding the insulation of the electrical connection.

FIG. 6 shows the electrode pole 1 of FIG. 1 implanted in the atrial septum 10 in further detail. In addition to the embodiment of FIG. 5, a second electrode pole surrounding the insulation of coil 6 is present. Electrode pole 1 is connected to the pacemaker/defibrillator via coil 6. The second pole is either the pacemaker pole (not shown) or a metallic coil with tip 9.

Figure 7:
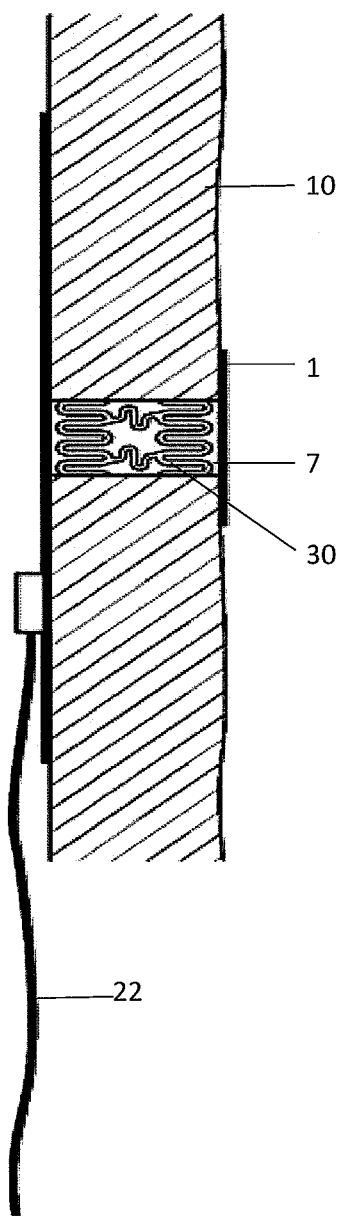
FIG. 7 is a detailed view of an alternate embodiment of the electrode pole of FIG. 1 having an electrode pole implanted in the atrial septum and further comprising a stent.

FIG. 7 shows the electrode pole 1 of FIG. 1 implanted in the atrial septum 10 with a stent 30 in the opening 7. The stent 30 is implanted thus allowing the expansion (ballooning) of the opening 7, if required. The electrode pole 1 is in shape of a double umbrella. The electrical connection of electrode pole 1 to the pacemaker/defibrillator is via cable 22.

Figure 8A:
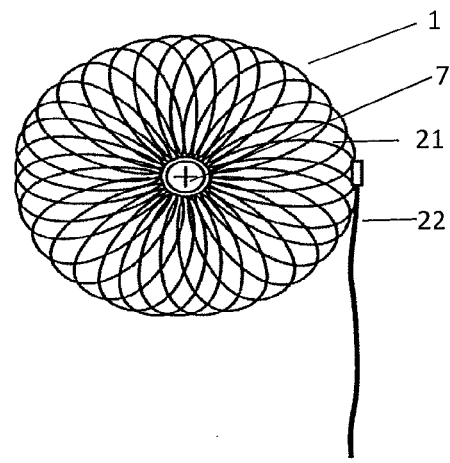
FIGS. 8a-8c are detailed views of the electrode pole of FIG. 1.
Figure 8B:
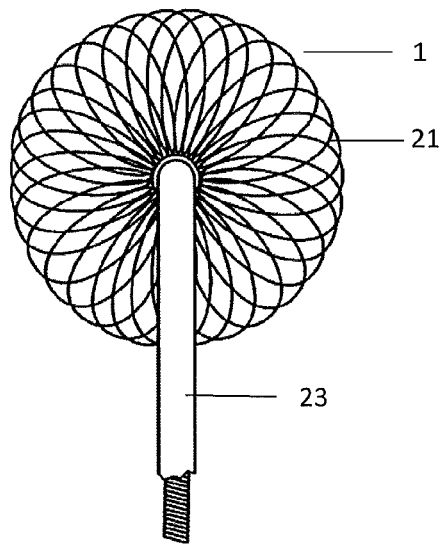
Figure 8C:
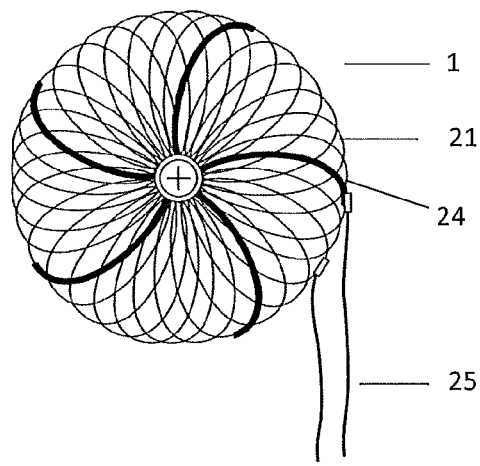

FIGS. 8a, 8b and 8c show the electrode pole 1 in detail. FIG. 8a shows the braiding in an umbrella like construction. The electrode pole 1 is formed from memory metal threads 21 for example, from Nitinol threads. The electrical connection of electrode pole 1 to the pacemaker/defibrillator is via cable 22. The opening 7 is in the center of the metal braiding allowing access to the left heart chambers.

FIG. 8b shows the braiding as in FIG. 8a with the opening 7 having a tube 23. The tube 23 is used for connecting the electrode pole 1 with a pacemaker/defibrillator. The braiding may consist of one single wire braiding or a double- or multi wire braiding and may have different sizes. If required, partly insulated braid members 24 may be present, as shown in FIG. 8c, resulting in a bipolar electrode which is connected via the two cables 25 to a pacemaker pole.

Figure 9A:
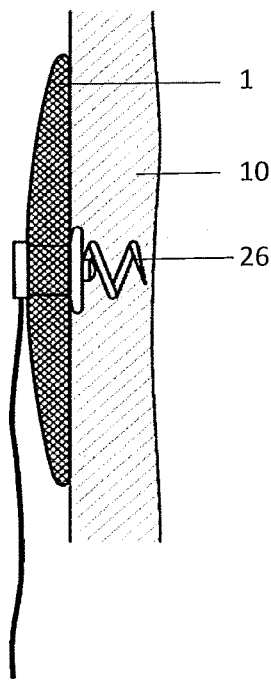
FIGS. 9a-9c are detailed views of alternate embodiments of electrode poles.
Figure 9B:
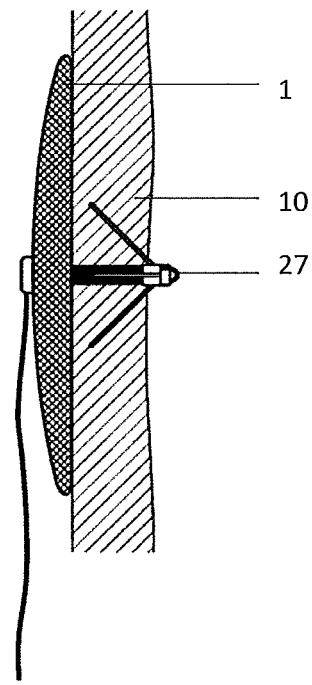
Figure 9C:
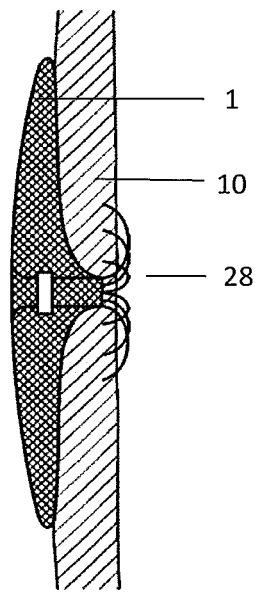

FIG. 9a-9c shows different means for attaching the electrode pole 1 in the septum 10. Attachment may be done by means of a screw coil 26 as shown in FIG. 9a or by means of a spread hook fastening element 27 as shown in FIG. 9b. In one embodiment, shown in FIG. 9c, the ends of the wires or threads are formed in such a manner that the ends hook within the septum when the insertion catheter is withdrawn.

In another embodiment, a magnet is mounted into the braiding of the electrode pole. In yet another embodiment, the braiding may be coated with a biocompatible polymer layer, preferably covered with silicone or polyurethane.

The methods and systems of the present invention, as described above and shown in the drawings, provide for an implantable indifferent reference electrode pole with superior properties. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. An implantable electrode device designed for heart stimulation and/or cardioversion/defibrillation in connection with a pacemaker or a defibrillator comprising:
   a large-surface area indifferent reference electrode pole configured to be permanently implanted in the atrial septum and in electrical communication with a pacemaker or defibrillator, the electrode pole made from biocompatible metal braiding and having a tube like opening,
   the electrical communication positioned from the pacemaker/defibrillator through the right atrium of the heart through the indifferent electrode pole into the left atrium through the opening, thus allowing electrical pulses to be delivered to the electrode pole and stimulating the heart.

2. The implantable electrode device according to claim 1, wherein the electrode pole is shaped like an occlusion element being self-expandable and forming a double disc which bridges the left and right atrium.

3. The implantable electrode device according to claim 1, wherein the opening of electrode pole has a proximal end and a distal end, the proximal end near the right atrium is attached to an elongated tube.

4. The implantable electrode device according to claim 3, wherein a stent is placed in the tube like opening.

5. The implantable electrode device according to claim 3, wherein the tube like opening comprises a seal member disposed within.

6. The implantable electrode device according to claim 5, wherein the seal member contains a drug formulation.

7. The implantable electrode device according to claim 3, wherein at least one coil is disposed within an inner part of the elongated tube.

8. The implantable electrode device according to claim 1, wherein the electrical communication to electrode pole is placed at the outer edge of the metal braiding.

9. The implantable electrode device according to claim 1, wherein the metal braiding of electrode pole is fitted with a fixation element in form of a screw coil.

10. The implantable electrode device according to claim 1, wherein the metal braiding of electrode pole is fitted with a fixation element in form of a spread hook fastening element.

11. The implantable electrode device according to claim 1, wherein at least one part of the metal braiding of electrode pole is coated with a biocompatible polymer layer.

12. The implantable electrode device according to claim 1, wherein a pacing electrode tip pole is inserted through the opening into the left atrium, the tip pole having a distal screw electrode such that the left atrium is stimulated between the electrode pole and the screw electrode.

* * * * *